United States Patent
Santa Cruz et al.

(10) Patent No.: US 6,558,364 B1
(45) Date of Patent: May 6, 2003

(54) SANITARY UNDERGARMENT

(76) Inventors: Cathy D. Santa Cruz, 7630 Tholl Dr., Reno, NV (US) 89506; Usha Mehta, 6649 Valley Wood Dr., Reno, NV (US) 89523

( * ) Notice: Subject to any disclaimer, the term of this patent is extended or adjusted under 35 U.S.C. 154(b) by 0 days.

(21) Appl. No.: 09/651,912

(22) Filed: Aug. 30, 2000

(51) Int. Cl.[7] .................... A61F 13/15; A61F 13/20
(52) U.S. Cl. .................... 604/385.05; 604/385.04; 604/385.14; 604/387; 604/395; 604/396; 604/398; 604/402
(58) Field of Search ............... 604/385, 385.03–385.05, 604/385.14, 386, 387, 389–402; 2/400–409

(56) References Cited

U.S. PATENT DOCUMENTS

| | | | | | |
|---|---|---|---|---|---|
| 1,283,632 A | * | 11/1918 | Beck | ............... | 604/397 |
| 1,772,969 A | * | 8/1930 | Takeuchi | ............... | 604/397 |
| 2,026,158 A | * | 12/1935 | Bennett | ............... | 604/398 |
| 2,530,719 A | * | 11/1950 | Neal | ............... | 604/397 |
| 2,627,859 A | * | 2/1953 | Hargrave | ............... | 604/398 |
| 2,705,957 A | * | 4/1955 | Mauro | ............... | 604/398 |
| 2,842,129 A | * | 7/1958 | Ernstorff | ............... | 604/398 |
| 3,460,538 A | * | 8/1969 | Behna | ............... | 604/397 |
| 3,489,149 A | * | 1/1970 | Larson | ............... | 604/397 |
| 3,599,638 A | * | 8/1971 | Rickard | ............... | 604/398 |
| 3,636,951 A | * | 1/1972 | Glasgow | ............... | 604/398 |
| 3,714,946 A | * | 2/1973 | Rudes | ............... | 604/398 |
| 4,072,150 A | * | 2/1978 | Glassman | ............... | 604/389 |
| 4,352,256 A | * | 10/1982 | Tong | ............... | 604/398 |
| 4,605,408 A | * | 8/1986 | Lassen | ............... | 604/386 |
| 4,695,279 A | * | 9/1987 | Steer | ............... | 604/397 |
| 5,037,418 A | * | 8/1991 | Kons et al. | ............... | 604/585.05 |
| 5,221,275 A | * | 6/1993 | Van Iten | ............... | 604/382 |
| 5,651,779 A | * | 7/1997 | Burrell | ............... | 604/398 |
| 5,711,034 A | * | 1/1998 | Cillik | ............... | 2/406 |

FOREIGN PATENT DOCUMENTS

| | | | | |
|---|---|---|---|---|
| DE | 1516462 | * | 6/1969 | ............ 604/396 |
| FR | 0653177 | * | 3/1929 | ............ 604/395 |
| GB | 017249 | * | 2/1908 | ............ 604/402 |
| GB | 1144674 | * | 3/1969 | ............ 2/406 |
| IT | 0280448 | * | 7/1934 | ............ 604/395 |

\* cited by examiner

*Primary Examiner*—Aaron J. Lewis
*Assistant Examiner*—K. M. Reichle

(57) ABSTRACT

A sanitary undergarment which is usable with an absorbent pad having lateral extension wings thereon. The undergarment having a first and a second crotch portion between which the lateral extension wings can be inserted and held in a secure manner by adhesive. The undergarment can be boxer shorts or a panty.

1 Claim, 5 Drawing Sheets

SANITARY UNDERGARMENT

FIELD OF THE INVENTION

The present invention relates generally to sanitary underwear especially suitable for use with absorbent articles such as sanitary napkins, panty liners, and incontinence pads. More specifically, the present invention is most suitable for use with those absorbent articles that have underwear covering components commonly known as wings or side wrapping elements that are normally folded in between the wearers thighs and positioned externally on the underwear when the underwear is pulled up.

BACKGROUND OF THE INVENTION

Absorbent articles such as sanitary napkins, panty-liners, and incontinence pads are devices that are typically worn in the crotch region of underwear. These devices are designed to absorb and retain liquid and other discharges from the human body and to prevent body and clothing soiling. Sanitary napkins are a type of absorbent article worn by women with their underwear that is normally positioned between the wearer's legs, adjacent to the perineal area of the body. Sanitary napkins both with and without side flaps (or wings) are disclosed in the literature and are available in the marketplace.

Generally when sanitary napkins are provided with flaps, the flaps extend laterally from a central absorbent means and are intended to be folded around the edges of the wearer's panties in the crotch region. Commonly, the flaps are provided with an attachment means for either affixing the flaps to the underside of the wearer's panties or to the opposing flap. The flaps are generally effective for preventing exudates from soiling the edges of the wearer's panties.

While sanitary pads having flaps are commonly viewed as providing better protection against soiling as compared to sanitary pads without flaps, some women find applying sanitary pads having flaps to be inconvenient for various reasons. For instance, some women find it to be difficult to attach the flaps to the underside of the crotch of their panties. This can be due to factors such as the tendency for the adhesive fasteners on the flaps to stick to themselves or to other parts of the sanitary napkin. Furthermore, the adhesive fasteners on the flaps also have a tendency to come unglued after an extended use and get stuck on the wearer's skin. As a result, some women still prefer a sanitary napkin without flaps. Some women who generally prefer a sanitary napkin with flaps, occasionally (such as during periods of light flow) prefer a sanitary napkin without flaps. The patent literature provides several variations of sanitary pads having conventional flaps that attempt to solve some of these problems. Following are some of the examples:

U.S. Pat. No. 4,911,701 issued to Mavinkurve
U.S. Pat. No. 5,125,918 issued to Seidy
U.S. Pat. Nos. 5,154,715 and 5,221,275 issued to Van Iten
U.S. Pat. No. 4,940,462.

Furthermore, numerous sanitary undergarments have also been provided in prior art. For example, U.S. Pat. No. 4,022,212 to Lovison; U.S. Pat. No. 4,560,381 to Southwell; U.S. Pat. No. 4,690,681 to Haunschild et al.; U.S. Pat. No. 4,813,950 to Branch; U.S. Pat. No. 4,880,424 to Rautenberg and U.S. Pat. No. 5,098,419 to Gold; Roberts; U.S. Pat. No. 5,546,607 to Mary K.; U.S. Pat. No. 5,944,708 to Philpott T.; all are illustrative of such prior art. While these units may be suitable for the particular purpose to which they address, they do not attempt to solve the problems associated with sanitary pads with wings.

SUMMARY

A need exists for a hygienic underwear that is comfortable, attractive and appropriate for use by adult and adolescent women and is similar in general appearance and feel to conventional panties. In particular, a need exists for an underwear which can conveniently and efficiently solve the problems faced by the wearer when attempting to attach the wings or flaps of a sanitary pad to the underside of the wearer's panties. Furthermore, there exists a need for an underwear that provides a way to keep the flaps tucked in place for a long time, away from the wearers skin, while still providing the protection of side flaps. Furthermore, there also exists a need for underwear which reduces shifting of the sanitary pad with wings to a minimum when worn by the wearer.

The present invention is sanitary underwear used with an absorbent article, such as a sanitary napkin that has a pair of panty covering components (or side wrapping elements). The present invention is especially meant to provide coverage to the wearer's panties to reduce staining of the edges of the panty crotch (or side soiling) when the underwear is pulled up adjacent to the wearer's body.

Another object of the present invention is to provide underwear which is worn with an absorbent article, such as a sanitary napkin with wings or flap extensions and provide coverage to the wearer's panties to reduce side soiling (i.e., staining of the edges of the panty crotch).

It is another object of the present invention to provide underwear to be used with an absorbent article, such as a sanitary napkin with flaps that folds around the sides of the wearer's panties yet away from the wearer's skin.

It is yet another object of the present invention to provide underwear that allows the wings or the flaps in a sanitary pad to fold around the sides of the wearer's panties for an extended period of time.

It is still another object of the present invention to provide a underwear that reduces crumpling and other types of transverse deformation usually experienced by the wearer of a sanitary napkin with wings.

These and other objects of the present invention will be more readily apparent when considered in reference to the following description and when taken in conjunction with the accompanying drawings.

BRIEF DESCRIPTION OF THE DRAWINGS

While the specification concludes with claims particularly pointing out and distinctly claiming the subject matter which is regarded as forming the present invention, it is believed that the invention will be better understood from the following description when taken in conjunction with the accompanying drawings in which:

DETAILED DESCRIPTION OF THE DRAWINGS

Referring now in detail to the drawings wherein like characters correspond to like elements throughout the various views.

Figure 1:
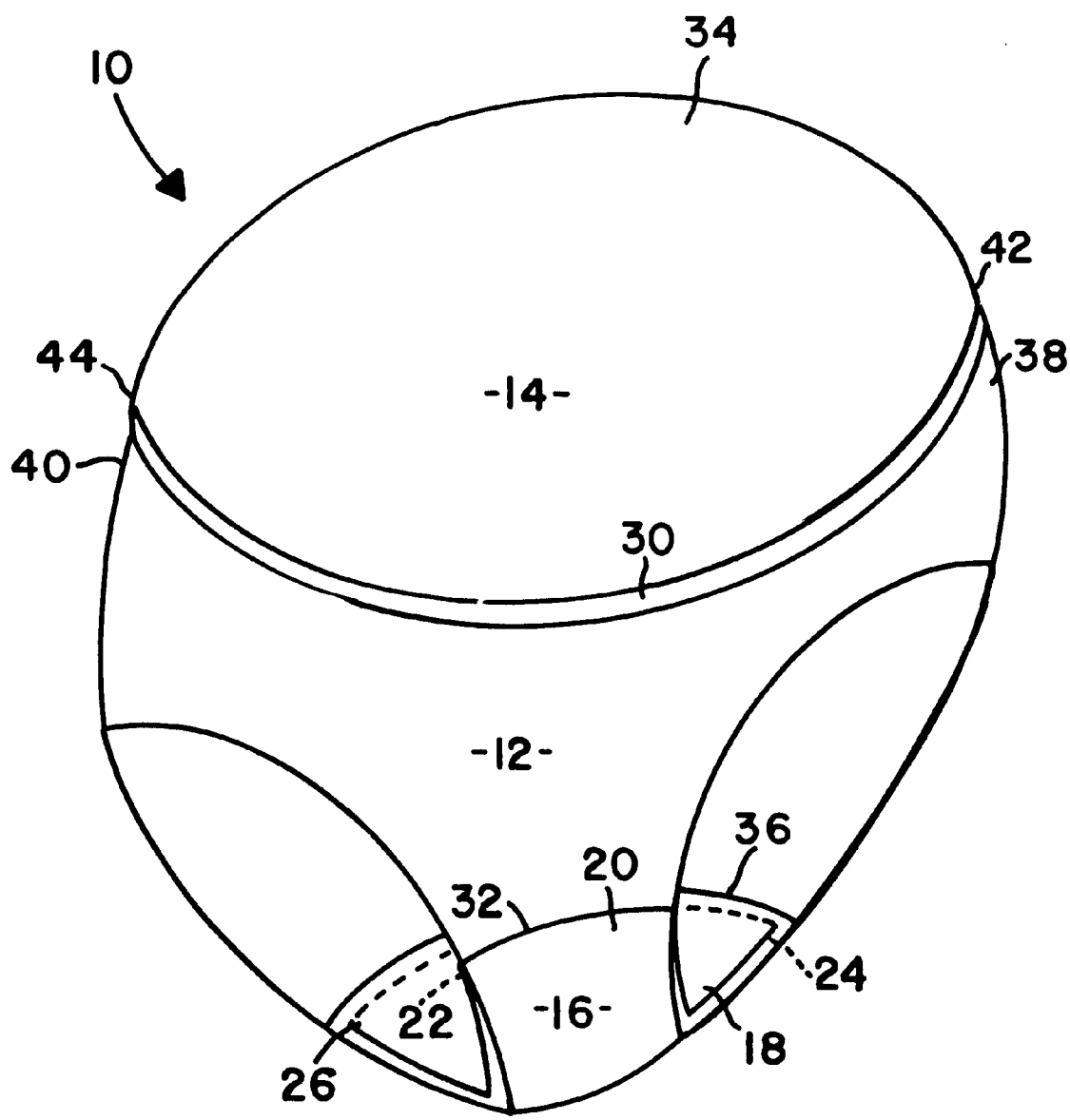
FIG. 1 is a perspective overview of the preferred embodiment for the present invention.

In FIG. 1 is shown the preferred embodiment for the present invention wherein (10) represents a sanitary undergarment, such as a panty, which is formed from a front body portion (12), a rear body portion (14), an external crotch portion (16) and an internal crotch portion (18), with external crotch portion (16) and internal crotch portion being substantially of the same shape and size.

It is to be understood that sanitary undergarment or panty (10) can be made from any suitable material of engineering choice, such as cotton, Nylon, SPANDEX, or the like and is made in various sizes of choice. It is to be also understood that such undergarments are usually sewn together by stitching, which not only prevents fraying but also is a suitable fastening means. Thus, the present invention is to be fastened together in the same manner but for clarity purposes of the drawings we do not show typical stitching or other type of fastening means, but it is to be inherent.

Even though undergarments such as panties are well known, the following specification will clarify complete construction of the preferred embodiment for the undergarment (10) as illustrated in FIGS. 1–6. Wherein, external crotch portion (16) is shown having a first end (20) and a second end (24), and internal crotch portion (18) is shown having a first end (22) and a second end (26). The first end (20) of external crotch portion (16) is fixedly attached to first end (22) of internal crotch portion (18), such as by stitching (not shown). The second end (24) of external crotch portion (16) is fixedly attached to second end (26) of internal crotch portion (18), such as by stitching (not shown). Therefore, it can now be seen external crotch portion (16) and internal crotch portion (18) in combination form an internal opening (28).

Further construction of undergarment (10) or panty, includes a front body portion (12) having an upper waist section (30) and a lower crotch attachment section (32). A rear body portion (14) is shown having an upper waist section (34) and a lower crotch attachment section (36). The lower crotch attachment section (32) of front body portion (12) is fixedly attached to each first end (20 & 22), such as by stitching (not shown), and the lower crotch attachment section (36) of rear body portion (14) is fixedly attached to each second end (24 & 26), such as by stitching (not shown), thereby, attaching each body portion (12 & 14) to each crotch portion (16 & 18).

Further construction of undergarment (10) or panty, includes front body portion (12) having a first side section (38) and a second side section (40) and rear body portion (14) having a first side section (42) and a second side section (44). The first side section (38) of front body portion (12) is fixedly attached to the first side section (42) of rear body portion (14), such as by stitching (not shown), and the second side section (40) of front body portion (12) is fixedly attached to the second side section (44) of rear body portion (14), such as by stitching (not shown).

It can now be seen that each portion (12,14,16, & 18) in combination form a sanitary undergarment (10) which is substantially in the shape of a panty, with the panty having an internal opening (28) between each crotch portion (16&18).

Figure 2:
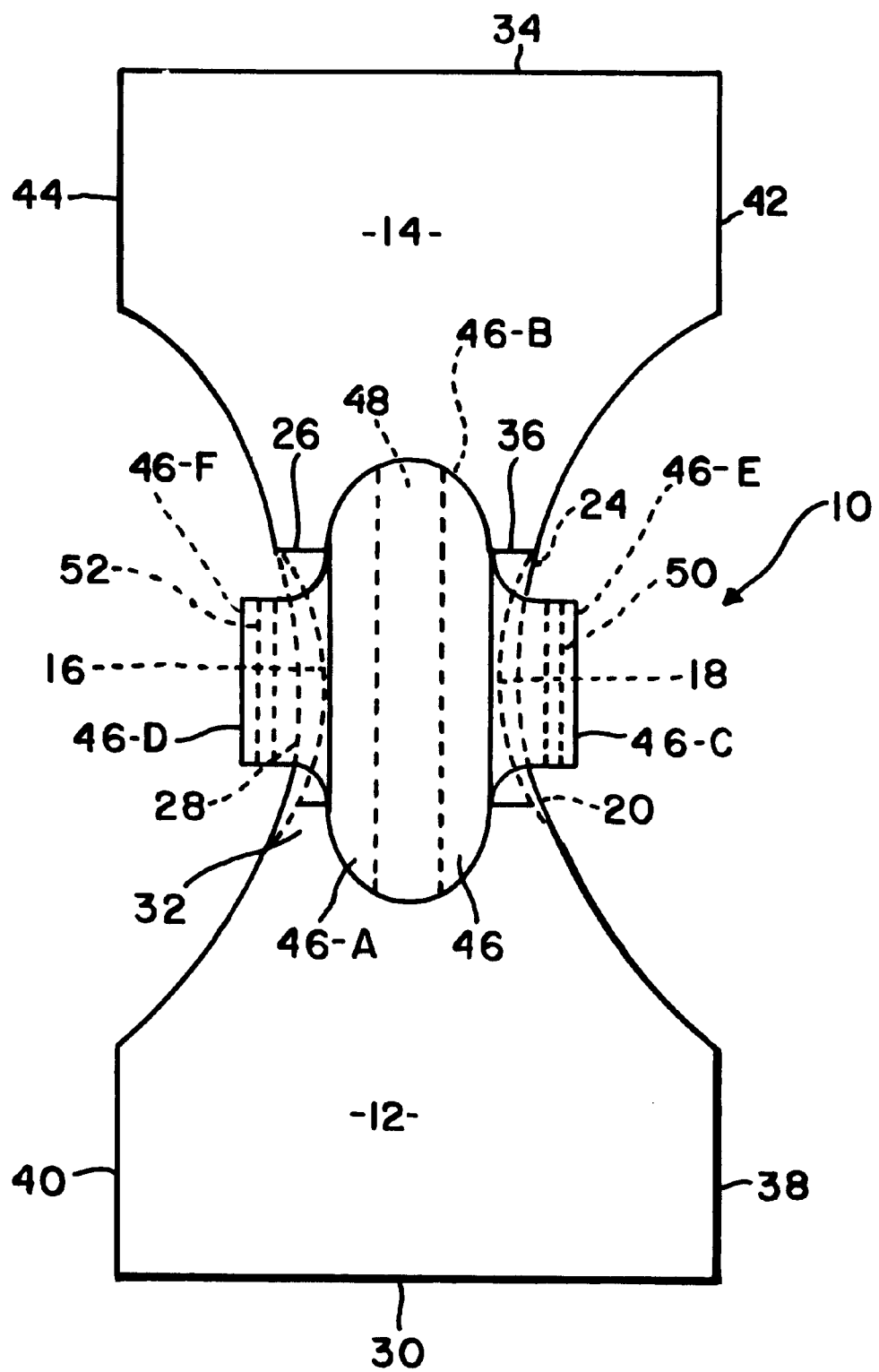
FIG. 2 is a plan view for the present invention showing an absorbent pad in an open position.
Figure 3:
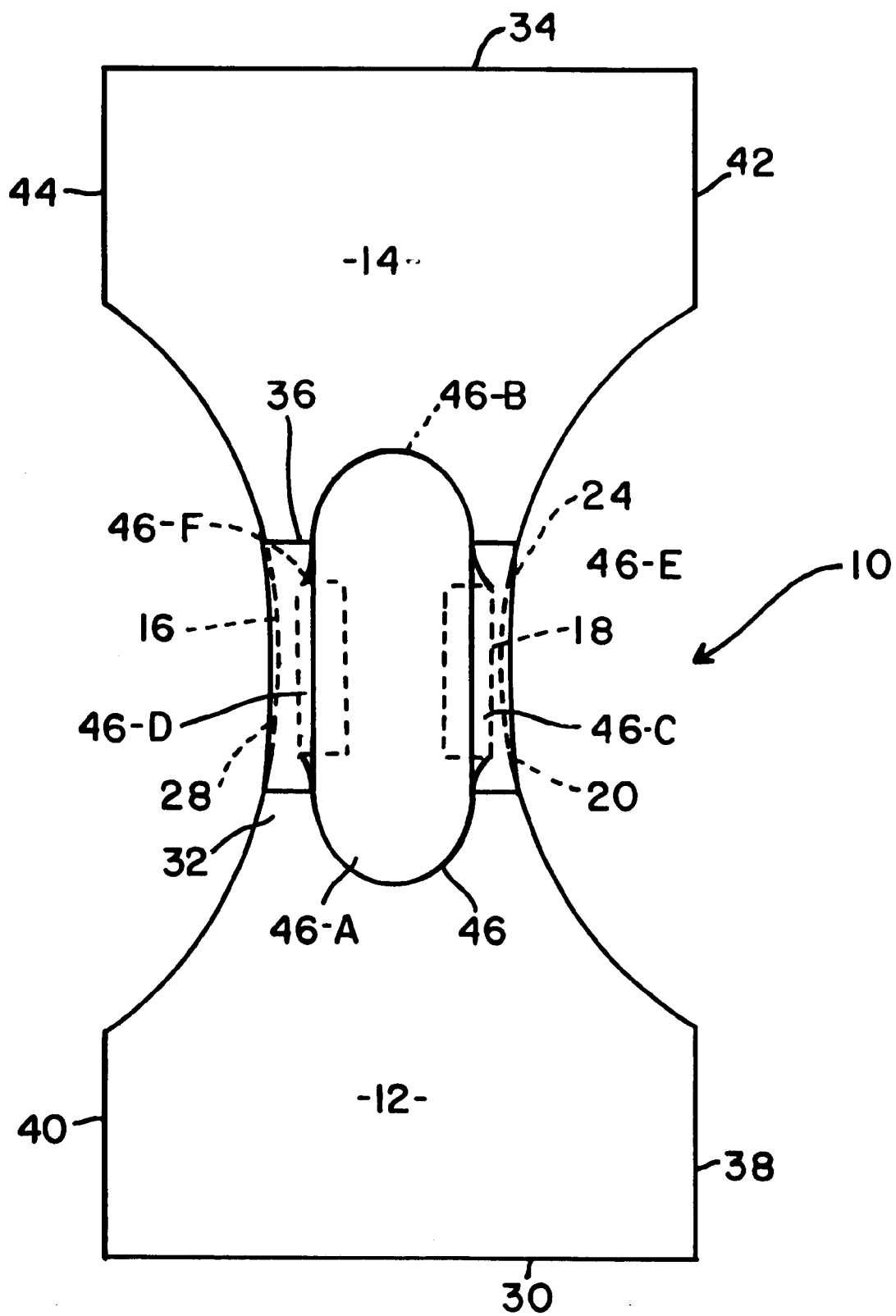
FIG. 3 is a plan view for the present invention showing an absorbent pad in a closed position.
Figure 4:
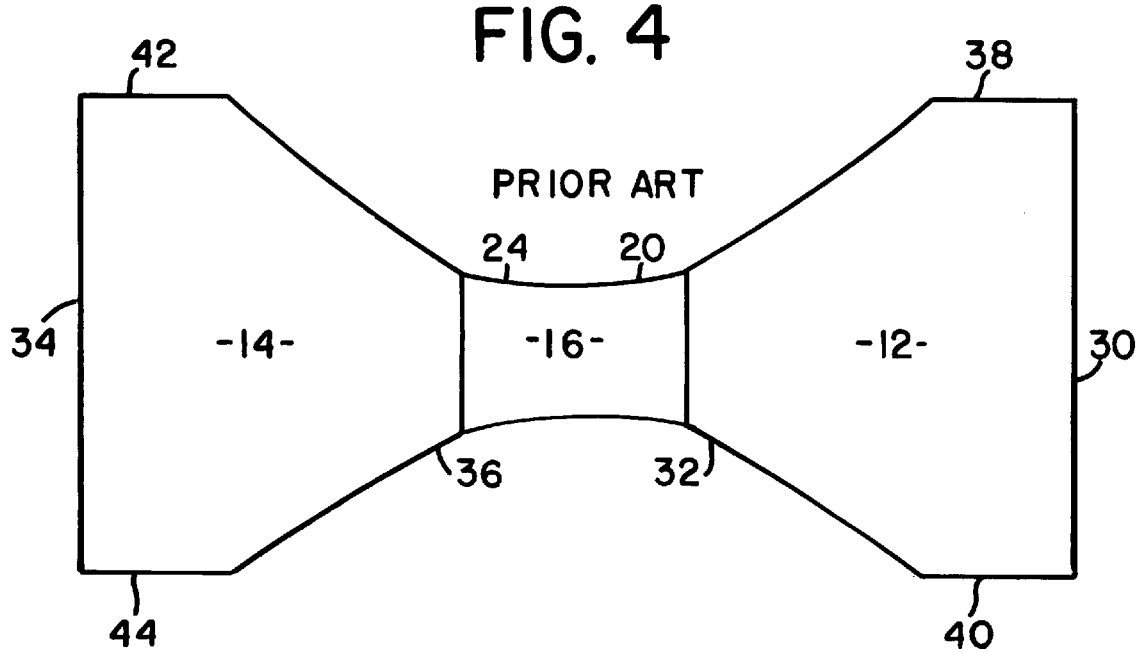
FIG. 4 is an overview of the known prior art.
Figure 5:
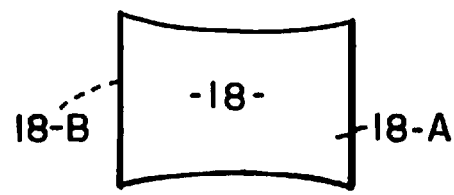
FIG. 5 is a top view of an internal crotch portion.
Figure 6:
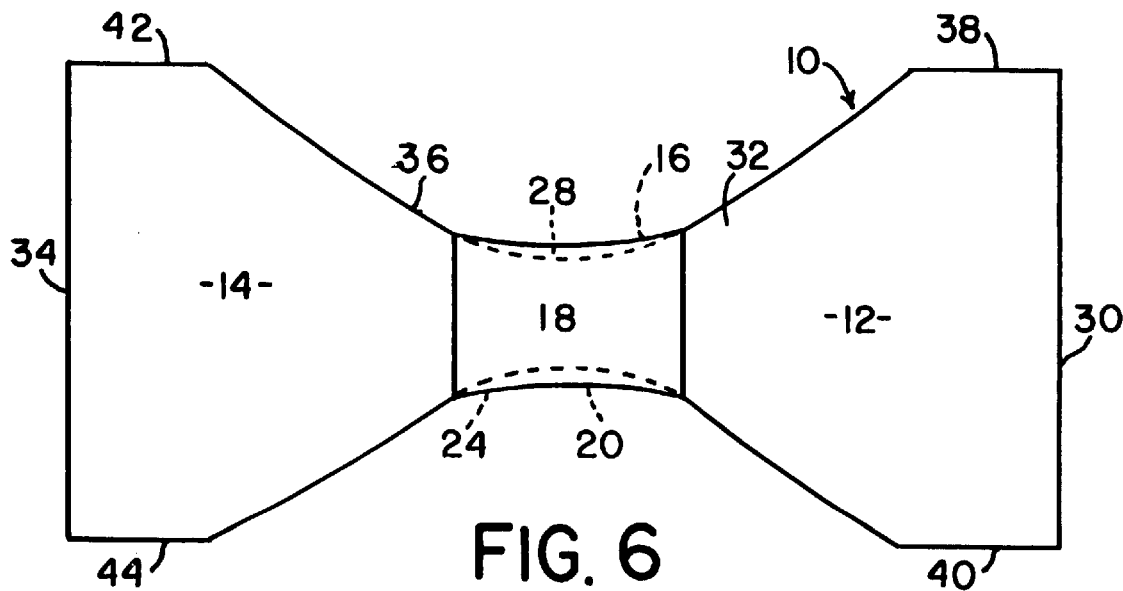
FIG. 6 illustrates the internal crotch portion when attached onto a prior art panty.

Referring now to FIGS. 2–6 which substantially represent a plan view for the present invention. In FIGS. 2 & 3, we show an absorbent pad (46) which can be substantially any typical prior art menstrual pad of choice such as those produced by KOTEX, STAYFREE, etc., or other types of suitable pads may include typical in continence pads such as those produced by DEPEND. Still further another suitable type of pad may include a diaper having wings, although none are apparently available on the market today.

However, there is a preference for an absorbent pad such as depicted herein, wherein the absorbent pad (46) includes a top surface (46-A), a bottom surface (46-B), a first lateral wing extension (46-C) and a second lateral wing extension (46-D), each lateral wing extension (46-C & 46-D) being substantially opposed to each other.

Bottom surface (46-B) of absorbent pad (46) has an adhesively attached removable strip (48) thereon which is shown in ghost lines. First lateral wing extension (46-C) has a bottom surface (46-E), and second lateral wing extension (46-D) has a bottom surface (46-F). Bottom surface (46-E) of first lateral wing extension (46-C) has an adhesively attached removable strip (50) which is shown in ghost lines in FIG. 2, and bottom surface (46-F) of second lateral wing extension (46-D) has is adhesive covered by a removable strip (52) which is shown in ghost lines in FIG. 2.

It is to be noted that FIG. 2 represents a plan view as the absorbent pad (46) before each strip (48, 50 & 52) has been removed and illustrates a first position. While FIG. 3 represents a plan view of the absorbent pad (46) after each strip (48, 50 & 52) has been removed and illustrates a second position.

It will now be seen when each removable strip (48, 50 & 52) is removed, then the bottom surface (46-B) of absorbent pad (46) can be easily positioned onto the top surface (18-A) of internal crotch portion (18) and held in a secure manner by adhesive. It is to be noted, for clarity purposes within the drawings, top surface (18-A) and bottom surface (18-B) are only shown in FIG. 5. Thereafter, each lateral wing extension (46-C & 46-D) can then be folded and inserted into internal opening (28) as depicted in FIG. 3 whereby bottom surface (46-E & 46-F) of each lateral wing extension (46-C & 46-D) is now secured onto bottom surface (18-B) of internal crotch portion (18).

Figure 7:
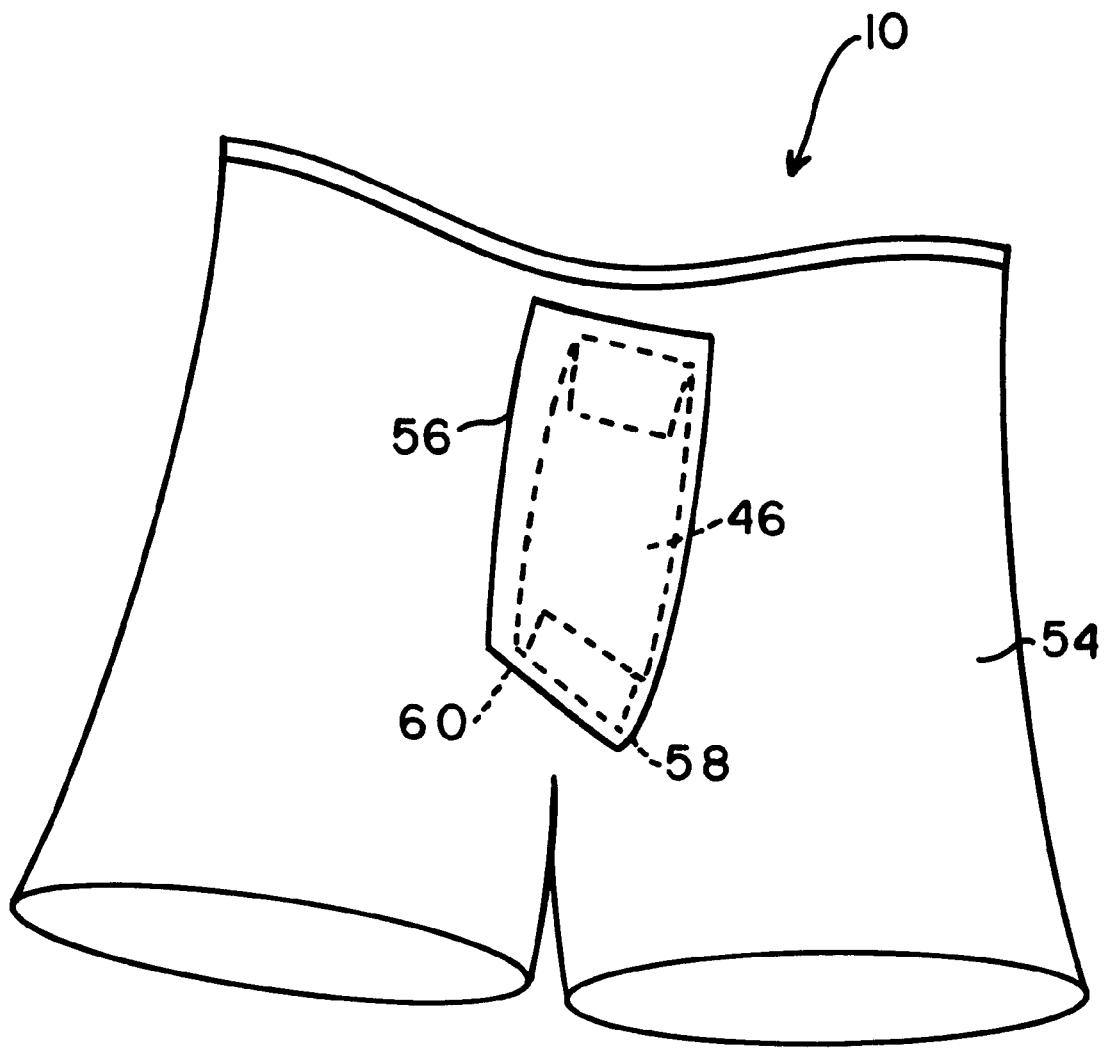
FIG. 7 illustrates a perspective overview of a second embodiment for the present invention.

It is to be understood that the present invention may include additional embodiments. For example, a second embodiment is shown in FIG. 7 which represents an embodiment which would be most suitable for men, or boys who have medical problems such as incontinence problems, or the like. Whereby, the present invention is formed into a pair of typical boxer shorts. The actual construction of the boxer shorts (54) is not disclosed or addressed as the construction of such shorts is very well known. However, the following specification teaches how the present pair of boxer shorts differs from the known prior art.

In FIG. 7 is shown a pair of boxer shorts (54) having an external fly portion (56) and an internal fly portion (58) with external fly portion (54) and internal fly portion (58) in combination forming an internal opening therebetween. Again it is to be noted that any type of suitable absorbent pad of user choice may be used, but the pad (46) as taught herein is preferred. The user can easily remove previously described strips (48, 50 & 52) and then position and adhesively attach pad (46) at a location of choice upon internal fly portion (58).

After folding each lateral wing extension (46-C & 46-D) each wing extension (46-C & 46-D) is inserted into internal opening (60) between internal fly portion (58) and external fly portion (56). The absorbent pad (46) and lateral wing extensions (46-C & 46-D) are now securely attached by adhesive to boxer shorts (54).

While particular embodiments of the present invention have been illustrated and described, it would be obvious to those skilled in the art that various other changes and modifications can be made without departing from the spirit and scope of the invention.

What I claim as new and wish to secure by Letters Patent is:

1. A sanitary undergarment and absorbent pad in combination comprising: a front body portion; a rear body portion; an external crotch portion; an internal crotch portion; and an absorbent pad; said external crotch portion and said internal crotch portion being of the same shape and size, said external crotch portion having a first end and a second end, said internal crotch portion having a first end and a second end, said first end of said external crotch portion being fixedly attached to said first end of said internal crotch portion, said second end of said external crotch portion being fixedly attached to said second end of said internal crotch portion, said external crotch portion and said internal crotch portion in combination forming an internal opening, said front body portion having an upper waist section and a lower crotch attachment section, said rear body portion having an upper waist section and a lower crotch attachment section, said lower crotch attachment section of said front body portion being fixedly attached to each said first end, said lower crotch attachment section of said rear body portion being fixedly attached to each said second end, said front body portion having a first side section and a second side section, said rear body portion having a first side section and a second side section, said first side section of said front body portion being fixedly attached to said first side section of said rear body portion, and said second side section of said front body portion being fixedly attached to said second side section of said rear body portion, said internal crotch portion having a top surface and a bottom surface, said absorbent pad comprising: a top surface; a bottom surface; a first lateral wing extension; and a second lateral wing extension; each said extension being opposed to each other, said bottom surface of said absorbent pad having an adhesive covered by a removable strip, said first lateral wing extension having a bottom surface, said second lateral wing extension having a bottom surface, said bottom surface of said first lateral wing extension having an adhesive covered by a removable strip, said bottom surface of said second lateral wing extension having an adhesive covered by a removable strip, whereby:

each said strip is removed and said bottom surface of said absorbent pad is said top surface of said internal crotch portion and held in a secure manner by said adhesive thereon, with each said lateral wing extension then being folded and inserted into said internal opening, whereby:

said bottom surface of each said lateral wing extension is secured by said adhesive thereon to said bottom surface of said internal crotch portion within said internal opening.

\* \* \* \* \*